United States Patent [19]

Sakurai et al.

[11] 4,269,187

[45] May 26, 1981

[54] TAMPON

[75] Inventors: Akira Sakurai, Sakura; Yoshimi Tsuchiya; Hiroshi Mizutani, both of Yachiyo, all of Japan

[73] Assignee: Kao Soap Co., Ltd., Tokyo, Japan

[21] Appl. No.: 83,741

[22] Filed: Oct. 11, 1979

[30] Foreign Application Priority Data

Nov. 2, 1978 [JP] Japan .............................. 53/135298

[51] Int. Cl.³ .............................................. A61F 15/00
[52] U.S. Cl. ..................................... 128/263; 128/285
[58] Field of Search ........................ 128/263, 270, 285

[56] References Cited

U.S. PATENT DOCUMENTS

| 2,829,646 | 4/1958 | Kurkjian | 128/263 |
| 3,059,642 | 10/1962 | Gershen | 128/263 |
| 3,101,713 | 8/1963 | Sargent | 128/263 |
| 3,628,533 | 12/1971 | Loyer | 128/263 |

FOREIGN PATENT DOCUMENTS 700840 12/1964 Canada ...................................... 126/263

Primary Examiner—John D. Yasko
Attorney, Agent, or Firm—Blanchard, Flynn, Thiel, Boutell & Tanis

[57] ABSTRACT

A tampon comprises an applicator having an outer cylinder and an absorbent material push-out portion and an absorbing material contained in said applicator, characterized in that the inner diameter of the rear end portion of said outer cylinder is smaller than the inner diameter of the barrel portion of said cylinder and said absorbent material push-out portion has a cavity in the center thereof and comprises a push-out top end contained in said outer cylinder and an inserting supporting piece connected to said push-out top end and folded outwardly from outer cylinder.

3 Claims, 12 Drawing Figures

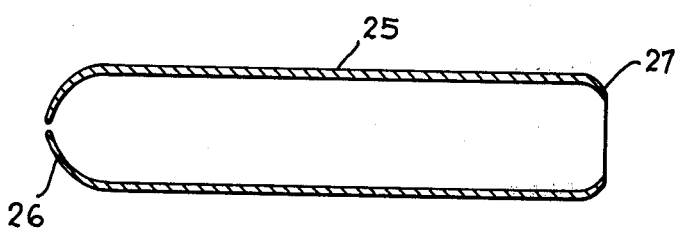
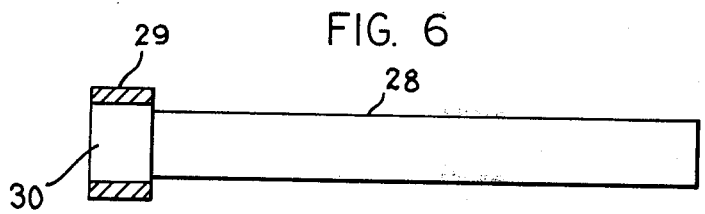
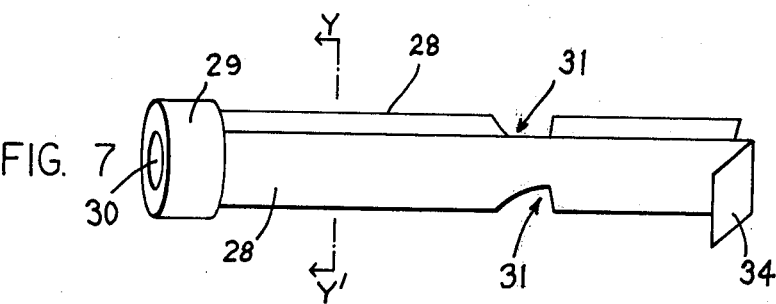
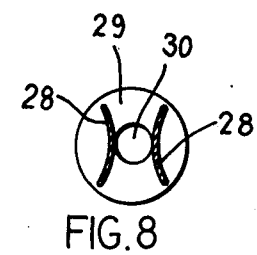
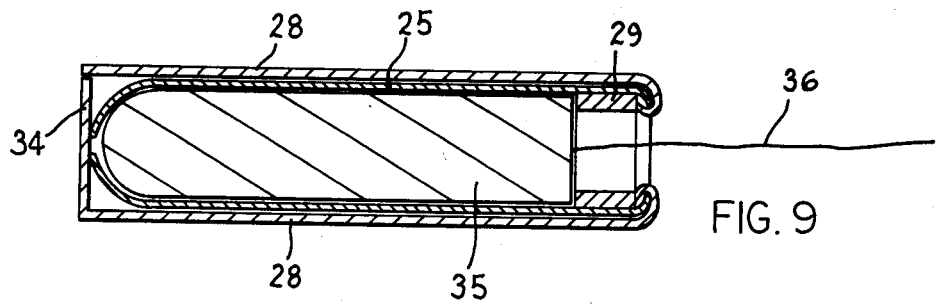

ial has been marketed. In this tampon, an outer cylinder 18 and
TAMPON

BACKGROUND OF THE INVENTION

1. FIELD OF THE INVENTION

The present invention relates to a hygienic tampon for the menses.

2. DESCRIPTION OF PRIOR ARTS

Napkins have heretofore occupied the main current of hygienic articles for the menses, but the demand for tampons has recently been increasing. The following three types of tampons have heretofore been proposed and marketed.

(1) Finger type:

Typically, an absorbent material formed by compression-molding an absorbent such as absorbent cotton or the like is used. A tampon of this type is characterized that when it is actually used, an overlapping material is completely removed and an inner absorbent material is inserted into the body by fingers of the user per se. A largest advantage of the tampon of this type is that the size can be diminished. More specifically, the size of the tampon of this type is much smaller than that of an ordinary napkin and it can be carried in a handbag or the like. However, when it is actually used, the absorbent material is inevitably touched by the hand of the user and it must be inserted by fingers which inevitably touch unsanitary areas before insertion. Therefore, the tampon of this type is not satisfactory from the sanitary viewpoint.

(2) Stick type:

An absorbing material similar to the absorbing material of the tampon of the type (1) is used, but an appropriate hole is formed in the tail portion of the absorbing material and one end of a stick-like tool composed of a paper or the like is set at this hole and the absorbent material is inserted into the body with the aid of this stick-like tool while operating the stick-like tool with the hand of the user. This type is improved over the above-mentioned type (1) from the sanitary viewpoint. However, since the stick-like inserting tool is very thin, the operation is not performed stably and the user inevitably has an unstable feeling in connection with the insertion state.

(3) Applicator type:

An inserting tool composed of a paper material, a plastic material or the like, which includes outer and inner cylinders capable of sliding relatively to each other, is employed, and an absorbent material is contained in the outer cylinder and is pushed out from the opening on the top end of the outer cylinder and inserted into the body by sliding the inner cylinder. The sanitary problem involved in the type (1) is solved substantially completely in this type. However, the tampon of this type is defective in that (1) falling-out of the inner cylinder is readily caused by insufficient connection between the inner and outer cylinders and (2) since a special inserting tool as described above is employed, the outer size of the tampon as a whole is very large and at least 2 times the length of the absorbent material and it is very troublesome to carry and handle the tampon.

The present invention relates to a tampon of the above-mentioned type (3). More particularly, the present invention relates to an improvement in a hygienic tampon for menses having a mechanism for inserting an absorbent material of the tampon into the body by using an inserting tool. In short, the present invention provides an applicator type tampon in which the foregoing defects involved in the conventional hygienic tampons are sufficiently eliminated.

Many tampons of the applicator type have heretobefore been proposed and typical instances will now be described in detail by reference to the accompanying drawings.

BRIEF DESCRIPTION OF THE DRAWINGS

FIG. 5 is a longitudinally sectional view showing an outer cylinder of an applicator that is used in the present invention.

FIG. 6 is a longitudinally sectional view illustrating an example of the absorbent material push-out portion of the applicator according to the present invention.

FIG. 7 is a perspective view illustrating another example of the absorbent material push-out portion of the applicator according to the present invention.

FIG. 8 is a view showing the section taken along the line Y—Y' in FIG. 7.

FIG. 9 is a longitudinally sectional view showing the state of the tampon of the present invention before the use.

SUMMARY OF THE INVENTION

Figure 1:
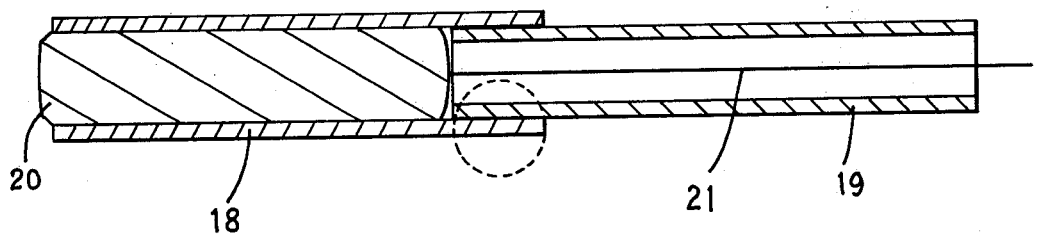
FIG. 1 is a longitudinally sectional view showing a conventional tampon including a paper applicator.
Figure 2:
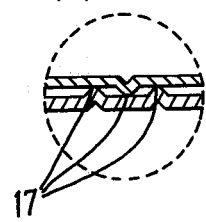
FIG. 2 is an enlarged view showing the cylinder connection portion in the tampon shown in FIG. 1.

According to one prior art technique, a tampon including an applicator composed of a paper material has been marketed. In this tampon, an outer cylinder 18 and an inner cylinder 19 are arranged in a manner as shown in FIG. 1, and an absorbent material 20 is contained in the outer cylinder and a string 21 for taking out the absorbent material is extended to the outside of the outer cylinder. When the tampon is actually used, the outer cylinder 18 is inserted into the body and the inner cylinder 19 is slid toward the interior of the body to push out the absorbing material 20 into the body and complete the insertion. In order to prevent falling-out of the inner cylinder, in some tampons, projections 17 are formed by pressing the inner and outer cylinders as shown in an enlarged view of FIG. 2. Even by provision of such projections, however, no satisfactory effect of preventing falling-out of the inner cylinder can be attained. Furthermore, if such projections are formed, the length of the applicator is increased and is more than 2 times the length of the absorbing material, and there is brought about a defect that the bulk is very large when the tampon is worn.

Figure 3:
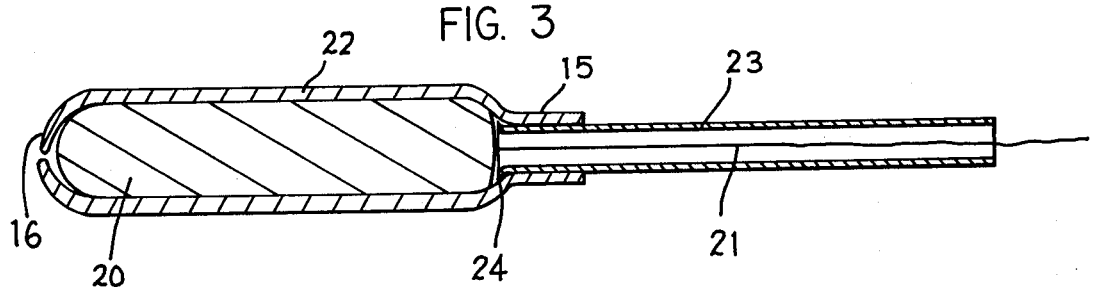
FIG. 3 is a longitudinally sectional view showing a conventional tampon including a plastic applicator.

Subsequently to tampons including a paper applicator, there have been marketed tampons including a plastic applicator as shown in FIG. 3.

Figure 4:
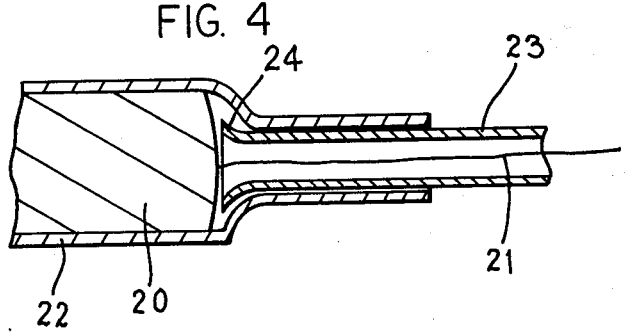
FIG. 4 is an enlarged view showing the cylinder connection portion in the tampon shown in FIG. 3.

In a tampon shown in FIG. 3, a petal-like projection 16 of an outer cylinder 22 is shaped in the semi-spherical form surrounding an absorbing material 20 and the diameter of a tail portion 15 of the outer cylinder 22 is slightly smaller than that of the barrel portion of the outer cylinder 22. The tampon further includes an inner cylinder 23 having a falling-out preventing top end 24 (see FIG. 4). When this tampon is actually used, the inner cylinder 23 is slid as in the case of the tampon shown in FIG. 1 and the absorbing material 20 is pushed out and inserted into the body to complete insertion.

In the tampon of this type, by rounding the top end of the outer cylinder, the feeling on insertion of the outer cylinder into the body is improved and the falling-out preventing effect is enhanced. However, the problem of a large bulk on wearing is left unsolved.

We made researches with a view to solving the foregoing problems involved in the conventional tampons of the applicator type, and as a result, we have now completed the present invention.

It is therefore a primary object of the present invention to provide a tampon characterized in that (1) it has a good sanitary effect, (2) the inner cylinder is not caused to fall out from the outer cylinder on wearing, (3) the size is diminished and (4) no unpleasant feeling is given on wearing.

In accordance with the present invention, there is provided an applicator type tampon comprising an applicator having an outer cylinder and an absorbent material push-out portion and an absorbing material contained in said applicator, characterized in that the inner diameter of the rear end portion of said outer cylinder is smaller than the inner diameter of the barrel portion of said cylinder and said absorbent material push-out portion has a cavity in the center thereof and comprises a push-out top end contained in said outer cylinder and an inserting supporting piece connected to said push-out top end and folded outwardly from said outer cylinder.

The present invention will now be described in detail by reference to embodiments illustrated in the accompanying drawings.

FIG. 5 is a longitudinally sectional view illustrating an example of the outer cylinder of the applicator according to the present invention. Referring to FIG. 5, an outer cylinder 25 is shaped so that the inner diameter of the rear end portion 27 of the outer cylinder 25 is smaller than the inner diameter of the barrel portion of the outer cylinder 25. By this arrangement, falling-out of an absorbent material or an absorbent material push-out portion is prevented. In order to reduce the resistance to insertion of the tampon into the vagina, it is preferred that the top end and 26 of the outer cylinder 25 be rounded.

The absorbent material push-out portion comprises a push-out top end 29 and an inserting supporting piece 28 connected to said top end 29, as shown in FIGS. 6 and 7. It is preferred that the push-out top end 29 be shaped to have a columnar form, but the top end may have an angular or semispherical shape so far as it has a function of transmitting the force imposed on the inserting supporting piece 28 to the absorbent material. It is indispensable that a through hole 30 should be formed in the push-out top end 29 and a string 36 for drawing out the tampon from the body should be passed through this hole 30 and extended to the outside. Since the inserting supporting piece 28 is required to have a rigidity sufficient to transmit the force, an arcuate shape as shown in FIG. 8 is preferable to a plate-like shape for the inserting supporting piece 28. For the preparation and application reasons, it is preferred that two inserting supporting pieces be formed, but the number of the inserting supporting pieces is not particularly critical in the present invention. As shown in FIG. 9, the absorbent material push-out portion is shaped so that the push-out top end 29 is contained in the outer cylinder 25 and the inserting supporting piece 28 is outwardly folded from the outer cylinder 25. By virtue of this characteristic feature, the size of the tampon can be remarkably diminished as compared with the sizes of the conventional tampons.

Figure 10:
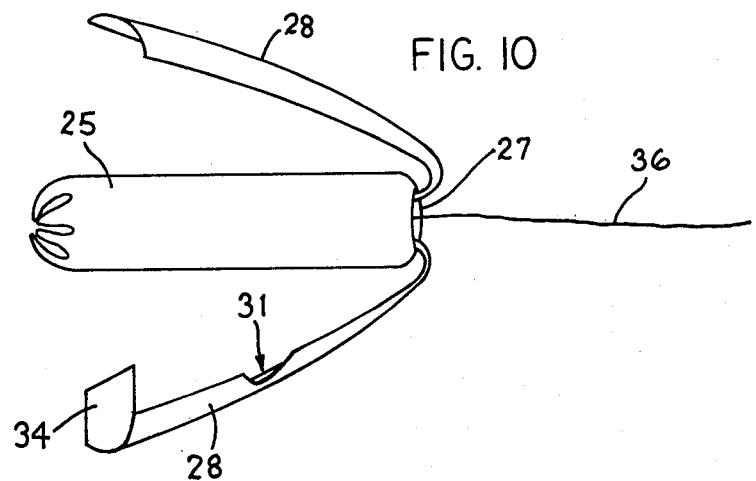
FIG. 10 is a perspective view showing the state of the tampon of the present invention at the time of preparation for insertion.
Figure 11:
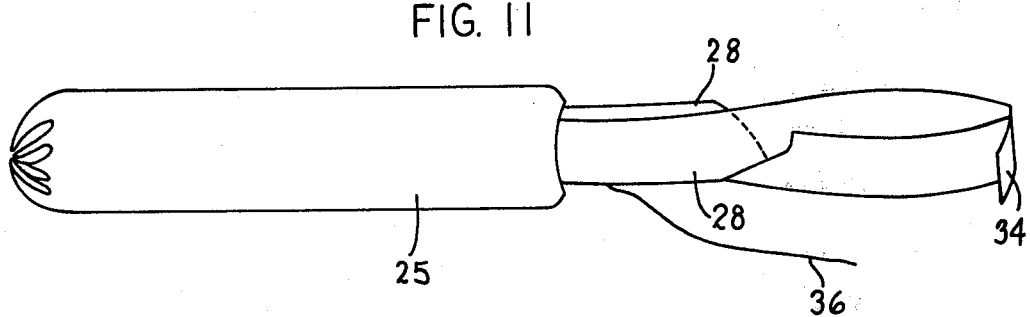
FIG. 11 is a perspective view showing the state of the tampon of the present invention just before the insertion.
Figure 12:
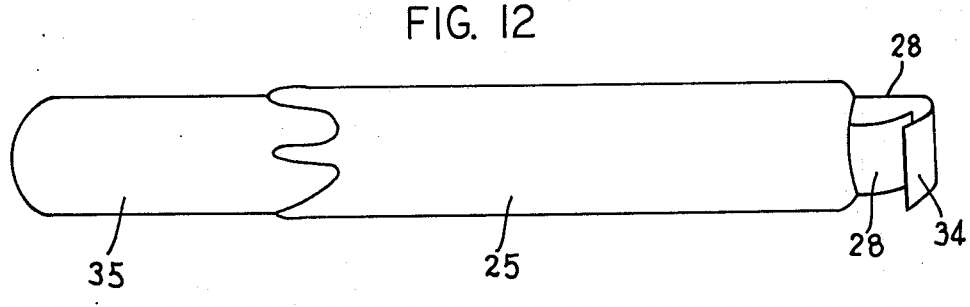
FIG. 12 is a perspective view showing the state of the tampon of the present invention after the insertion.

When the tampon of the present invention is actually used, as shown in FIGS. 10, 11 and 12, the folded part of the inserting supporting piece 28 is returned and the inserting supporting piece 28 is pressed, whereby the absorbent material push-out portion is forwardly slid and the absorbent material is pushed out to the interior of the body to complete the insertion. Since the force should be equally applied to the two inserting supporting pieces 28 at the pressing operation, notches 31 are formed at positions apart from the push-out top end 29 of the respective inserting supporting pieces 28 by the same distance, and when these notches 31 are engaged with each other as shown in FIG. 11, the pressing force is uniformalized and good results can be obtained. If a cover 34 for the top end of the outer cylinder 25 is formed on the top end of the inserting supporting piece 28, the insertion of the absorbent material 35 can be remarkably facilitated by pressing said cover 34 at the inserting operation.

The tampon of the present invention having the abovementioned structure is in a very good sanitary condition before the use and does not include a problem of insufficient connection between the outer and inner cylinders, which is inevitably caused in the conventional tampons. Moreover, in the tampon of the present invention, the size of the applicator can be remarkably diminished and it is about ½ of the size of the applicator in the conventional tampons, and the defect of a large bulk on wearing can be eliminated. Furthermore, when the tampon of the present invention is actually used, only by a simple operation of sliding the absorbent material push-out portion forwardly, the applicable state can be attained. Accordingly, the tampon of the present invention gives various advantages to users.

What is claimed is:

1. A tampon comprising an applicator having an outer cylinder and an absorbent material push-out portion and an absorbing material contained in said applicator, characterized in that the inner diameter of the rear end portion of said outer cylinder is smaller than the inner diameter of the barrel portion of said cylinder and said absorbent material push-out portion has a cavity in the center thereof and comprises a push-out top end contained in said outer cylinder and an inserting supporting piece connected to said push-out top end and folded outwardly from said outer cylinder.

2. A tampon as set forth in claim 1 wherein said absorbent material push-out portion comprises two inserting supporting pieces and notches to be engaged with each other are formed on said inserting supporting pieces at positions apart from said push-out top end by the same distance.

3. A tampon as set forth in claim 2 wherein the top end of said outer cylinder is covered with said inserting supporting pieces.

* * * * *